(12) United States Patent
Shvetsov et al.

(10) Patent No.: US 12,390,575 B2
(45) Date of Patent: Aug. 19, 2025

(54) APPARATUS AND METHOD FOR FILTERING

(71) Applicant: Buffalo Filter LLC, Lancaster, NY (US)

(72) Inventors: Kyrylo Shvetsov, Depew, NY (US); Gregory Pepe, Lancaster, NY (US); Samantha Bonano, Williamsville, NY (US)

(73) Assignee: Buffalo Filter LLC, Lancaster, NY (US)

( * ) Notice: Subject to any disclaimer, the term of this patent is extended or adjusted under 35 U.S.C. 154(b) by 1023 days.

(21) Appl. No.: 17/261,900

(22) PCT Filed: Nov. 21, 2019

(86) PCT No.: PCT/US2019/062636
§ 371 (c)(1),
(2) Date: Jan. 21, 2021

(87) PCT Pub. No.: WO2020/106970
PCT Pub. Date: May 28, 2020

(65) Prior Publication Data
US 2022/0347372 A1    Nov. 3, 2022

Related U.S. Application Data

(60) Provisional application No. 62/770,486, filed on Nov. 21, 2018.

(51) Int. Cl.
*A61M 1/00* (2006.01)
*A61B 17/34* (2006.01)
(Continued)

(52) U.S. Cl.
CPC .......... *A61M 1/79* (2021.05); *A61B 17/3421* (2013.01); *A61B 17/3423* (2013.01);
(Continued)

(58) Field of Classification Search
CPC ............ A61B 17/3421; A61B 17/3423; A61B 2217/005; A61B 2218/008; A61B 17/34;
(Continued)

(56) References Cited

U.S. PATENT DOCUMENTS

| | | | |
|---|---|---|---|
| 4,619,672 A | 10/1986 | Robertson | |
| 6,592,543 B1* | 7/2003 | Wortrich | A61B 18/00 604/35 |

(Continued)

FOREIGN PATENT DOCUMENTS

| | | |
|---|---|---|
| CN | 101370420 A | 2/2009 |
| CN | 203315068 U | 12/2013 |

(Continued)

OTHER PUBLICATIONS

International Search Report for PCT/US2019/062636 completed Dec. 31, 2019, mailed Jan. 16, 2020.

*Primary Examiner* — Brigid K Byrd
(74) *Attorney, Agent, or Firm* — Timothy W. Menasco, Esq.; Harter Secrest & Emery LLP

(57) ABSTRACT

Embodiments of the present disclosure provide an apparatus and method for evacuation. An exemplary apparatus includes a trocar comprising an inlet at a distal end and an exit port at a proximal end, the inlet and the exit port are fluidly connected by a tubular hollow body circumscribing a cavity extending through a longitudinal axis of the trocar, the trocar includes a filter maintained within the cavity operable to filter at least one of fluid and particulates from a flow passing through the cavity. The apparatus further includes a vacuum source fluidly connected to the exit port, the vacuum source operable to pull at least one of fluid and particulates through the inlet, the cavity and the exit port.

12 Claims, 3 Drawing Sheets

Figure 1:
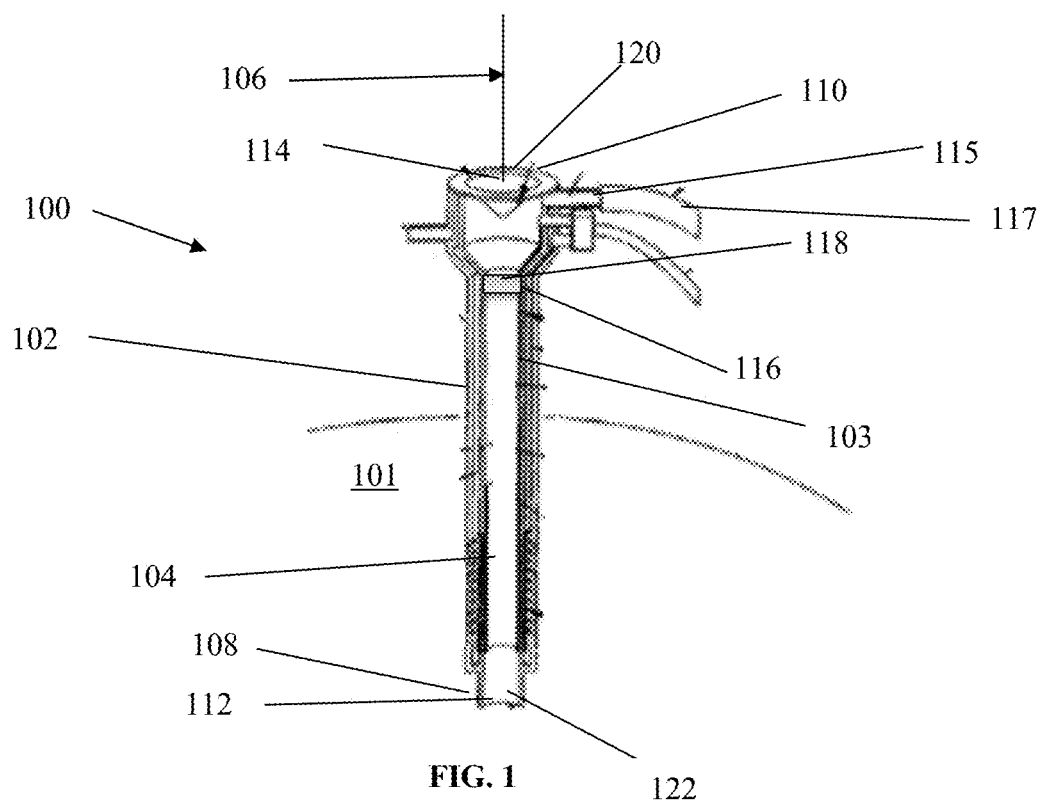

(51) Int. Cl.
  *B01D 46/00* (2022.01)
  *B01D 46/10* (2006.01)
  *B01D 46/54* (2006.01)

(52) U.S. Cl.
  CPC ..... *B01D 46/0002* (2013.01); *B01D 46/0047* (2013.01); *B01D 46/10* (2013.01); *B01D 46/543* (2013.01); *A61B 2217/005* (2013.01); *A61B 2218/008* (2013.01)

(58) Field of Classification Search
  CPC . A61M 1/79; B01D 46/0002; B01D 46/0047; B01D 46/10; B01D 46/543
  See application file for complete search history.

(56) References Cited

U.S. PATENT DOCUMENTS

| | | | |
|---|---|---|---|
| 2002/0128603 A1 | 9/2002 | Booth et al. | |
| 2008/0082084 A1 | 4/2008 | Roberts et al. | |
| 2012/0165610 A1 | 6/2012 | Poll et al. | |
| 2014/0088491 A1 | 3/2014 | Azarbarzin et al. | |
| 2014/0165842 A1* | 6/2014 | Bonano ................ | A61M 5/165 55/467 |
| 2014/0213992 A1 | 7/2014 | Ehlert | |
| 2016/0000459 A1 | 1/2016 | Palmerton et al. | |
| 2017/0303964 A1 | 10/2017 | Kellner et al. | |
| 2018/0140324 A1 | 5/2018 | Stearns et al. | |
| 2018/0214197 A1 | 8/2018 | Hiraga et al. | |
| 2018/0228510 A1* | 8/2018 | Holsten ............. | B01D 46/0097 |
| 2019/0328983 A1* | 10/2019 | Malkowski ......... | A61M 13/003 |
| 2019/0365404 A1* | 12/2019 | Ryan, Jr. ............ | A61B 17/0218 |
| 2021/0267639 A1* | 9/2021 | Fischer ............... | A61M 13/003 |

FOREIGN PATENT DOCUMENTS

| | | |
|---|---|---|
| CN | 103732266 A | 4/2014 |
| CN | 204562392 U | 8/2015 |
| CN | 205994569 U | 3/2017 |
| CN | 107970061 A | 5/2018 |
| CN | 109276308 A | 1/2019 |
| CN | 111315421 A | 6/2020 |
| CN | 112236093 A | 1/2021 |
| EP | 3316946 A1 | 5/2018 |
| JP | H06(1994)-178780 A | 6/1994 |
| JP | 2002204829 A | 7/2002 |
| JP | 2017502703 A | 1/2017 |
| JP | 2018126512 A | 8/2018 |
| WO | 2017057065 A1 | 4/2017 |
| WO | 2017066720 A1 | 4/2017 |
| WO | 2017184876 A1 | 10/2017 |
| WO | 2019084108 A1 | 5/2019 |
| WO | 2020087007 A1 | 4/2020 |

* cited by examiner

200: providing trocar comprising an inlet at a distal end and an exit port at a proximal end, the inlet and the exit port are fluidly connected by a tubular hollow body circumscribing a cavity extending through a longitudinal axis of the trocar, the trocar includes a filter maintained within the cavity operable to filter at least one of fluid and particulates from a flow passing through the cavity; and (b) providing a vacuum source fluidly connected to the exit port, the vacuum source operable to pull at least one of fluid and particulates through the inlet, the cavity and the exit port

202: wherein the trocar and the vacuum source is operable to provide a positive pressure flow rate through the inlet, the cavity and the exit port of between 0 mmHg to 22 mmHg

204: wherein the filter comprises a filter media membrane.

206: wherein the filter is comprised of at least one of fiber, glass, and non-woven materials

208: wherein the trocar passively allows a flow of the at least one of fluid and particulates through the inlet, the cavity, and the exit port when the vacuum source is not creating a vacuum.

210: wherein the filter further comprises a liquid trap and a filter media.

212: wherein the exit port comprises a gasket operable to allow a flow of the least one of fluid and particulates in a first position and obstruct a flow of the at least one of fluid and particulates in a second position

FIG. 2

APPARATUS AND METHOD FOR FILTERING

BACKGROUND OF THE INVENTION

Field of the Invention

Embodiments of the present disclosure relate generally to an apparatus and method for evacuation. The embodiments of the present disclosure relate more particularly to an apparatus and method for evacuation of smoke and particulates during medical procedures.

Description of Related Art

During a medical procedure surgical smoke, plume and/or aerosol can be created. This can occur when a laser or electrosurgical energy is delivered to a cell. When this occurs heat is created. This heat vaporizes the intracellular fluid, which can increase the pressure within the cell. The pressure can cause the cell membrane to burst. When the cell membrane bursts, a plume of smoke containing gas including water vapor is released into the atmosphere of the location of the medical procedure. Simultaneously, the heat created may char the protein and other organic matter within the cell. This can cause thermal necrosis in cells adjacent to the cell with the collapsed membrane. The charring of cells may also release other harmful contaminants into the atmosphere. Examples of such contaminants include carbonized cell fragments and gaseous hydrocarbons.

BRIEF SUMMARY OF THE INVENTION

In view of the foregoing, it is an object of the present disclosure to provide a method and apparatus for evacuation.

A first exemplary embodiment of the present disclosure provides an apparatus for evacuation. The apparatus includes a trocar including an inlet at a distal end and an exit port at a proximal end, the inlet and the exit port are fluidly connected by a tubular hollow body circumscribing a cavity extending through a longitudinal axis of the trocar, the trocar includes a filter maintained within the cavity operable to filter at least one of fluid and particulates from a flow passing through the cavity. The apparatus further includes a vacuum source fluidly connected to the exit port, the vacuum source operable to pull at least one of fluid and particulates through the inlet, the cavity and the exit port.

A second exemplary embodiment of the present disclosure provides a method of providing. The method includes providing trocar comprising an inlet at a distal end and an exit port at a proximal end, the inlet and the exit port are fluidly connected by a tubular hollow body circumscribing a cavity extending through a longitudinal axis of the trocar, the trocar includes a filter maintained within the cavity operable to filter at least one of fluid and particulates from a flow passing through the cavity. The method further includes providing a vacuum source fluidly connected to the exit port, the vacuum source operable to pull at least one of fluid and particulates through the inlet, the cavity and the exit port.

A third exemplary embodiment of the present disclosure provides a trocar assembly. The trocar assembly includes a hollow body having longitudinal axis bound by a distal end and a proximal end, the hollow body defining a cavity extending through the longitudinal axis of the hollow body. The trocar assembly further includes an inlet disposed at the distal end, and an exit port disposed at the proximal end, the exit port fluidly connected to inlet by the cavity. The trocar assembly still further includes a filter holder disposed within the cavity, the filter holder operable to maintain a filter media.

The following will describe embodiments of the present disclosure, but it should be appreciated that the present disclosure is not limited to the described embodiments and various modifications of the disclosure are possible without departing from the basic principles. The scope of the present disclosure is therefore to be determined solely by the appended claims.

BRIEF DESCRIPTION OF THE SEVERAL VIEWS OF THE DRAWING(S)

FIG. 1 presents a perspective view of an exemplary device suitable for use in performing exemplary embodiments of the present disclosure.

FIG. 2 presents a logic flow diagram in accordance with a method and apparatus for performing exemplary embodiments of the present disclosure.

Figure 3:
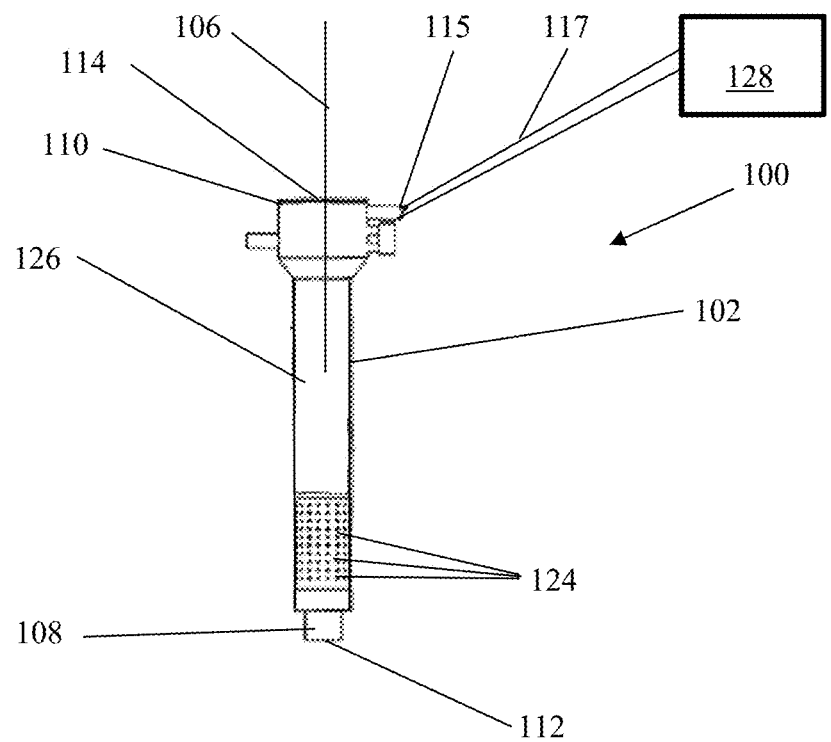

FIG. 3 presents a side view of an exemplary device suitable for use in performing exemplary embodiments of the present disclosure.

Figure 4:
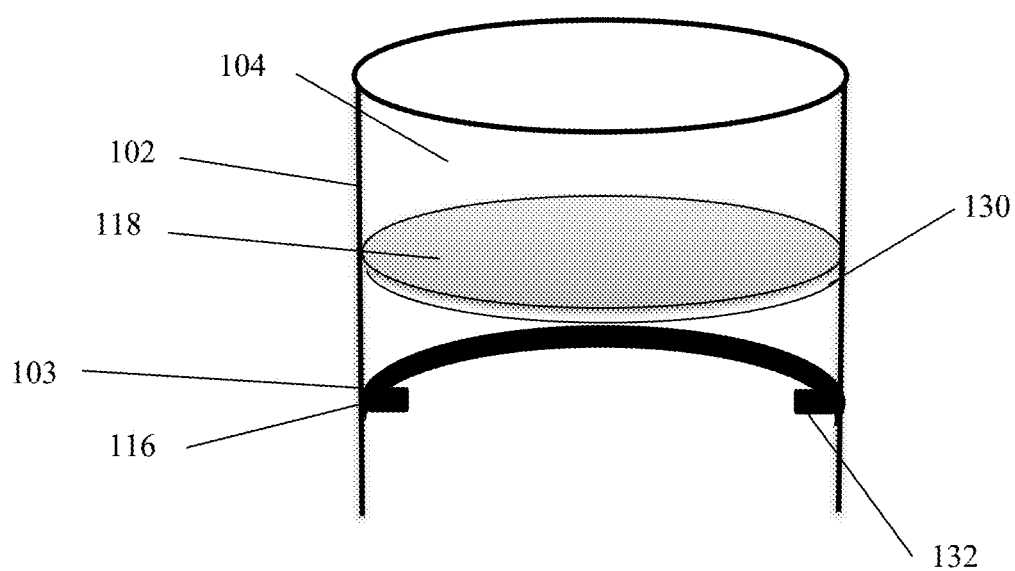

FIG. 4 presents a close-up cross-sectional view of an exemplary device suitable for use in performing exemplary embodiments of the present disclosure.

DETAILED DESCRIPTION OF THE INVENTION

Embodiments of the present disclosure provide a trocar assembly fluidly coupled to a vacuum source operable to evacuate gas, smoke, fluids and/or particulates from a surgical area or cavity, such as a body cavity. Embodiments provide that the trocar assembly is operable to be placed partially within a body cavity and when coupled to a vacuum source can evacuate smoke, fluids and/or particulates from the body cavity. Embodiments further provide that the trocar assembly is operable to be placed partially within a body cavity and is operable to passively allow fluid, smoke, gas, and/or particulates to pass through the trocar assembly. Embodiments of trocar assembly is operable to evacuate smoke, fluid and/or particulates by both pressure provided by the body cavity and pressure provided by an external vacuum source. Embodiments of trocar assembly is operable to filter out fluid, contaminants, smoke and/or particulates from a flow that passes through a hollow cavity within trocar assembly. Embodiments provide that trocar assembly is operable to provide a positive flow rate pressure between 0 mmHg to 20 mmHg and allows a leak rate of 0 liters to 12 liters. Embodiments of vacuum source is operable to provide vacuum pressure between 100 mmHg to 600 mmHg.

Referring to FIG. 1 shown is an exemplary trocar assembly 100 in accordance with embodiments of the present disclosure. Trocar assembly 100 includes a hollow body 102 defining a cavity 104, and a longitudinal axis 106 bound by a distal end 108 and a proximal end 110. Hollow body 102 includes a radial exterior surface 126 (shown in FIG. 3) and a radial interior surface 103. The radial interior surface 103 defines the outer most radial edge of cavity 104. The trocar assembly 100 includes an inlet 112 located at the distal end 108 of the trocar assembly 100. The inlet 112 provides a passageway from the outside environment to the cavity 104 within the hollow body 102. The trocar 100 also includes an exit port 114 located at the proximal end 110 of the trocar assembly 100. The exit port 114 provides a passageway from the cavity 104 within the hollow body 102 to the outside environment. The inlet 112, the cavity 104 and the exit port 114 are fluidly connected to one another such that gas, fluid and/or particulates are able to pass through the inlet 112, the cavity 104 and the exit port 114. Embodiments of trocar assembly 100 also include an outlet 115. Outlet 115 is fluidly connected to cavity 104 and inlet 112 such that gas, fluid and/or particulates are able to pass through the inlet 112, cavity 104 and outlet 115. As shown in FIGS. 1 and 3, outlet 115 can be fluidly connected to tube 117. In some embodiments, tube 115 is operably and fluidly connected to a vacuum source 128 (shown in FIG. 3) such that vacuum source 128 can urge, suction and/or evacuate fluid, gas and/or particulates through inlet 112, cavity 104, outlet 115 and tube 115. It should be appreciated that embodiments of vacuum source 128 also include the ability insufflate. In other words, vacuum source 128 is operable to create a flow of gas, fluid and/or particulates through inlet 112, cavity 104, outlet 115 and tube 117 in a direction toward or away from vacuum source 128.

Within the cavity 104 of the hollow body 102 of trocar assembly 100 is a filter holder 116. The filter holder 116 is operable maintain one or more a filters 118 operable to remove or filter out gas, fluid and/or particulates including smoke and other contaminates that pass through the cavity 104 and the filter 118. As shown in FIG. 4, embodiments of filter holder 116 include a rib, lip or rim 132 located along the radial interior surface 103 of body 102. Rib, lip or rim 132 provides a raised surface that circumscribes the radial interior surface 103 of body 102 at the same position within body 102 with respect to the longitudinal axis 106. In this regard, embodiments include all portions of filter 118 and filter holder 116, respectively, being equally spaced from the distal end 108. Embodiments include filter 118 and filter holder 116 being angled with respect to the longitudinal axis 106 such that a portion of filter 118 and filter holder 116 is closer to the distal end 108 than other portions of filter 118 and filter holder 116. In this embodiment, filter holder 116 creates a physical obstruction preventing movement of filter 118 within cavity 104. It should be appreciated that embodiments of filter holder 116 include one or more ribs, lips or rims such that filter 118 is secured in a particular location within cavity 104 thereby preventing movement of filter 118 when a flow of gas, fluid, and/or particulates pass through cavity 104 and filter 118.

Embodiments of filter 118 include a corresponding catch or channel 130 that is operable to interface with the rib, lip or rim 132 of filter holder 116 thereby creating a friction fit between filter 118 and filter holder 116. It should be understood that FIG. 4 depicts filter 118 and filter 116 being spaced from one another along the longitudinal axis 106 for purposes of illustrating the elements trocar assembly 100. However, in practice filter 118 with catch 130 can be located in contact with filter holder 116 and rib 132 such that catch 130 corresponds to rib 132. Embodiments of filter 118 thus provide that filter 118 and catch or ridge 130 is operable to flex such that filter 118 can be removeably and fixedly located within filter holder 116, but not flex or move to the extent that filter 118 moves during use. In other words, embodiments provide that filter 118 is operable to flex such that it can be fixedly placed in filter holder 116, but is also ridged enough to cause all gas, fluid, and/or particulates that pass from inlet 112 to outlet 115 or exit port 114 to also pass through filter 118 rather than around it.

It should also be appreciated that embodiments include filter 118 being fixedly and not removeably attached to filter holder 116. In this embodiment, filter 118 can be affixed to filter holder 116 and/or the radial interior surface 103 through the use of glue or other adhesive known in the art. Embodiments of the filter 118 include a filtration media membrane that is operable to allow a flow of gas through the filter 118, but is operable to trap particulates, certain types of gas and/or fluids. Embodiments of filter media include fiber, glass and non-woven materials.

The trocar assembly 100 includes a hollow body 102 with an inlet 112 for receiving air from an evacuator and/or insufflator. In this regard, trocar assembly 100 is operable to have air, gas, and/or fluids passed from an insufflator to outlet 115 through cavity 104 and out inlet 112 into a patient's body or surgical site 101. Trocar assembly 100 is also operable to air, gas, fluids, and/or particulates pass from a patient's body or surgical site 101 through inlet 112 through cavity 104 and out outlet 115. Trocar assembly is also operable to allow air, gas, and/or fluids to pass through the exit port 114, the cavity 104 and the inlet 112. The trocar 100 can include a tool entry port 120 with a one-way gasket disposed therein. The trocar 100 includes a tool exit port 122 at the distal end 108 of the trocar assembly 100. Embodiments of trocar assembly 100 include a plurality of holes or passageways 124 (shown in FIG. 3) located adjacent inlet 112 around the radial exterior surface 126 of body 102. Passageways 124 provide a passageway from the radial exterior surface 126 of body 102 to cavity 104 and exit port 114. It should be appreciated that embodiments of the present disclosure include trocar assembly 100 not having passageways 124 and having a uniform solid radial exterior surface 126 extending throughout the longitudinal axis 106 of body 102.

In practice, the trocar assembly 100 is inserted through an incision in a patient during a medical procedure to provide a pathway to a cavity inside the body of a patient. The insufflation air from vacuum source 128 passes through trocar assembly 100 into the cavity of the patient. A tool can also pass through trocar assembly 100 via exit port 114, cavity 104 and tool exit port 122, however, it should be appreciated that embodiments include trocar assembly 100 only being used for insufflation and/or evacuation of gas from the surgical site. The insufflation air from vacuum source 128 keeps the cavity in the patient pressurized to enlarge the surgical area for a surgical or diagnostic procedure conducted through an entry site. Surgical and/or diagnostic tools may be introduced into the cavity of the patient through the trocar 100. A scope inserted through the trocar 100 may provide imaging of the area inside the cavity.

An electrosurgical device may be inserted through the trocar 100 to enable the user to perform a surgical procedure inside the cavity of the patient. The removal of surgical smoke from the cavity of the patient may be desired in the case of electrocautery of electrosurgical procedures that produce surgical smoke.

Surgical smoke can be removed from the cavity of the patient through the cavity 104 of the trocar assembly 100. When vacuum source 128 is activated it can urge or suction gas, fluids and/or particulates to pass from the cavity within the patient through inlet 112, cavity 104, outlet 115 and tube 117. As the flow of gas, fluids, and/or particulates pass through cavity 104 they pass through filter 118 wherein filter 118 operably filters out particular gases, fluids and/or particulates from the flow. Alternatively, the exit port 114 or outlet 115 of the trocar assembly 100 can be maintained in an open position to allow a passive flow of gas from the cavity of the patient. In this embodiment, the passive flow of gas occurs because there is a pressure differential between the gas inside of the patient the surrounding atmosphere such that the higher pressure from within the cavity of the patient causes gas, fluids and/or particulates to flow from the cavity of the patient through trocar assembly 100 to the surrounding atmosphere.

For the embodiment that the outlet 115 of the trocar assembly 100 is connected to a vacuum source 128, the vacuum source 128 is operable to create a pressure urging a flow of fluid, smoke and/or particulates to pass through the inlet 112, the cavity 104 and the outlet 115 of the trocar assembly 100. Filter 118 can be permanently affixed to filter holder 116 within cavity 104 of trocar assembly 100 or can be removeably affixed to filter holder 116 prior to activation of vacuum source 128. Filter 118 is thus operable to remove contaminates, particulates and/or liquid from the flow. In the embodiment that trocar assembly 100 is not connected to a vacuum source, trocar assembly 100 is operable to allow a flow of fluid and/or particulates when the exit port 114 gasket is in an open position. In this embodiment trocar assembly 100 is operable to allow a flow until the internal pressure within the cavity of the patient reaches a predetermined threshold. Embodiments provide that exit port 114 can be configured to an open position, a closed position or an intermediate position wherein a flow is partially obstructed.

Reference is now made to FIG. 2, which presents a summary of the above teachings. Block 200 presents providing trocar comprising an inlet at a distal end and an exit port at a proximal end, the inlet and the exit port are fluidly connected by a tubular hollow body circumscribing a cavity extending through a longitudinal axis of the trocar, the trocar includes a filter maintained within the cavity operable to filter at least one of fluid and particulates from a flow passing through the cavity; and (b) providing a vacuum source fluidly connected to the exit port, the vacuum source operable to pull at least one of fluid and particulates through the inlet, the cavity and the exit port. Then block 202 specifies wherein the trocar and the vacuum source is operable to provide a positive pressure flow rate through the inlet, the cavity and the exit port of between 0 mmHg to 22 mmHg.

Following block 202, block 204 states wherein the filter comprises a filter media membrane. Block 206 relates wherein the filter is comprised of at least one of fiber, glass, and non-woven materials. Next, block 208 indicates wherein the trocar passively allows a flow of the at least one of fluid and particulates through the inlet, the cavity, and the exit port when the vacuum source is not creating a vacuum. Block 210 states wherein the filter further comprises a liquid trap and a filter media. Then block 212 specifies wherein the exit port comprises a gasket operable to allow a flow of the least one of fluid and particulates in a first position and obstruct a flow of the at least one of fluid and particulates in a second position.

The logic diagram on FIG. 2 may be considered to illustrate the operation of a method. The logic diagram may also be considered a specific manner in which components of a device are configured to be provided, whether such a device is an apparatus, a trocar assembly, a vacuum source, or one or more components thereof.

It is to be understood that any feature described in relation to any one embodiment may be used alone, or in combination with other features described, and may also be used in combination with one or more features of any other of the embodiments, or any combination of any other of the embodiments. Furthermore, equivalents and modifications not described above may also be employed without departing from the scope of the invention, which is defined in the accompanying claims.

This disclosure has been described in detail with particular reference to a presently preferred embodiment, but it will be understood that variations and modifications can be effected within the spirit and scope of the invention. The presently disclosed embodiments are therefore considered in all respects to be illustrative and not restrictive. The scope of the invention is indicated by the appended claims, and all changes that come within the meaning and range of equivalents thereof are intended to be embraced therein.

The invention claimed is:

1. An apparatus for evacuation, the apparatus comprising:
    a trocar comprising an inlet at a distal end, an outlet, and an exit port at a proximal end, the inlet, the outlet, and the exit port are fluidly connected by a tubular hollow body circumscribing a cavity extending through a longitudinal axis of the trocar, the trocar includes a filter maintained within the cavity operable to filter at least one of fluid and particulates from a flow passing through the cavity, wherein the filter further comprises a liquid trap operable to filter liquid and a filter media operable to filter particulate materials; and
    a vacuum source fluidly connected to the exit port, the vacuum source operable to pull at least one of fluid and particulates from the cavity through the inlet, the cavity and the outlet, wherein the trocar passively allows a flow of the at least one of fluid and particulates through the inlet, the cavity, and the outlet when the vacuum source is in an off position, wherein the trocar passively allows a flow of the at least one of fluid and particulates through the inlet, the cavity, and the exit port when the exit port is in an open position, and wherein the exit port is operable to allow a surgical tool to pass through the exit port to the cavity and the inlet.

2. The apparatus according to claim 1, wherein the trocar and the vacuum source are operable to provide a positive pressure flow rate through the inlet, the cavity and the exit port of between 0 mmHg to 22 mmHg.

3. The apparatus according to claim 1, wherein the filter media comprises a filter media membrane.

4. The apparatus according to claim 1, wherein the vacuum source is operable to provide pressure between 100 mmHg to 600 mmHg.

5. The apparatus according to claim 1, wherein the filter is comprised of at least one of fiber, glass, and non-woven materials.

6. The apparatus according to claim 1, wherein the outlet comprises a gasket operable to allow a flow of the least one of fluid and particulates in a first position and obstruct a flow of the at least one of fluid and particulates in a second position.

7. A method of forming, the method comprising:
    (a) forming a trocar comprising an inlet at a distal end, an outlet, and an exit port at a proximal end, the inlet and the exit port are fluidly connected by a tubular hollow body circumscribing a cavity extending through a longitudinal axis of the trocar, the trocar includes a filter maintained within the cavity operable to filter at least one of fluid and particulates from a flow passing through the cavity, wherein the filter further comprises a liquid trap operable to filter liquid and a filter media operable to filter particulate materials; and
    (b) connecting a vacuum source fluidly to the outlet, the vacuum source operable to pull at least one of fluid and particulates through the inlet, the cavity and the outlet, wherein the trocar passively allows a flow of the at least one of fluid and particulates through the inlet, the cavity, and the outlet when the vacuum source is in an off position, wherein the trocar passively allows a flow of the at least one of fluid and particulates through the inlet, the cavity, and the exit port when the exit port is in an open position, and wherein the exit port is operable to allow a surgical tool to pass through the exit port to the cavity and the inlet.

8. The method according to claim 7, wherein the trocar and the vacuum source are operable to provide a positive pressure flow rate through the inlet, the cavity and the exit port of between 0 mmHg to 22 mmHg.

9. The method according to claim 7, wherein the filter media comprises a filter media membrane.

10. The method according to claim 7, wherein the filter is comprised of at least one of fiber, glass, and non-woven materials.

11. The method according to claim 7, wherein the outlet comprises a gasket operable to allow a flow of the least one of fluid and particulates in a first position and obstruct a flow of the at least one of fluid and particulates in a second position.

12. A trocar assembly comprising:
a hollow body having a longitudinal axis bound by a distal end and a proximal end, the hollow body defining a cavity extending through the longitudinal axis of the hollow body;
an inlet disposed at the distal end;
an outlet disposed at the proximal end, the outlet fluidly connected to the inlet by the cavity;
an exit port disposed at the proximal end, the exit port fluidly connected to the inlet by the cavity; and
a filter holder disposed within the cavity, the filter holder operable to maintain a filter, wherein the filter further comprises a liquid trap operable to filter liquid and a filter media operable to filter particulate materials, and wherein the trocar assembly passively allows a flow of at least one of fluid and particulates through the inlet, the cavity, and the exit port when a vacuum source fluidly coupled to the exit port is in an off position, and wherein the trocar passively allows a flow of the at least one of fluid and particulates through the inlet, the cavity, and the exit port when the exit port is in an open position, and wherein the exit port is operable to allow a surgical tool to pass through the exit port to the cavity and the inlet.

* * * * *